United States Patent
Lacombe et al.

(10) Patent No.: US 7,402,545 B2
(45) Date of Patent: Jul. 22, 2008

(54) CATALYST THAT COMPRISES AT LEAST ONE BOG-STRUCTURED ZEOLITE AND ITS USE IN TRANSALKYLATION OF ALKYL-AROMATIC HYDROCARBONS

(75) Inventors: Sylvie Lacombe, Saint Genis Laval (FR); Emmanuelle Guillon, Saint Genis Laval (FR)

(73) Assignee: Institut Francais du Petrole, Rueil Maimaison Cedex (FR)

( * ) Notice: Subject to any disclaimer, the term of this patent is extended or adjusted under 35 U.S.C. 154(b) by 667 days.

(21) Appl. No.: 10/972,148

(22) Filed: Oct. 25, 2004

(65) Prior Publication Data

US 2005/0113618 A1    May 26, 2005

(30) Foreign Application Priority Data

Oct. 24, 2003    (FR)    ................... 03 12552

(51) Int. Cl.
*B01J 29/06*    (2006.01)
*C07C 5/22*    (2006.01)

(52) U.S. Cl. ............................. 502/74; 502/60; 502/63; 502/73; 423/700; 585/475

(58) Field of Classification Search ................ 423/700; 502/60, 63, 73, 74; 585/475
See application file for complete search history.

(56) References Cited

U.S. PATENT DOCUMENTS 5,552,033 A * 9/1996 Shih ............................. 208/89
5,952,536 A 9/1999 Nacamuli et al.
6,613,709 B1 * 9/2003 Merlen et al. ................. 502/64
2005/0234279 A1 * 10/2005 Serra et al. ................... 585/475
2006/0100471 A1 * 5/2006 Serra Alfaro et al. ........ 585/475

FOREIGN PATENT DOCUMENTS

EP    1077083 A    2/2001
FR    2821075 A    8/2002

OTHER PUBLICATIONS

J.J. Pluth and J.V. Smith, "Crystal structure of boggsite, a new high-silica zeolite with the first three-dimensional channel system bound by both 12- and 10- rings," American Mineralogist, vol. 75, 1990, pp. 501-507.

Adair Brian et al., "Reactions of meta-xylene on zeolites with intersecting medium and large pores. I. Basic studies," Microporous Materials, vol. 7, No. 5, Nov. 1996, pp. 261-270.

* cited by examiner

*Primary Examiner*—David M Brunsman
(74) *Attorney, Agent, or Firm*—Millen, White, Zelano, Branigan, P.C.

(57) ABSTRACT

This invention relates to a catalyst that contains at least one BOG-structured zeolite that comprises silicon and at least one Element T that is selected from the group that is formed by aluminum, iron, gallium and boron. The catalyst contains at least one metal that is selected from the group that is formed by the non-noble elements of groups VIB, VIIB and VIII of the periodic table. Said catalyst is used in a process for transalkylation of alkyl-aromatic hydrocarbons such as toluene and the alkyl-aromatic compounds with at least 9 carbon atoms.

20 Claims, No Drawings

CATALYST THAT COMPRISES AT LEAST ONE BOG-STRUCTURED ZEOLITE AND ITS USE IN TRANSALKYLATION OF ALKYL-AROMATIC HYDROCARBONS

TECHNICAL FIELD

This invention relates to a new catalyst that can be used, for example, in the reactions for transformation of aromatic hydrocarbons. More specifically, it relates to a catalyst that is used for the transalkylation of alkyl-aromatic hydrocarbons, and preferably transalkylation of toluene and aromatic compounds containing at least 9 carbon atoms, to produce xylenes. This invention also relates to the preparation of said catalyst as well as its use in a process for transalkylation of alkyl-aromatic hydrocarbons.

PRIOR ART

Numerous catalysts for dismutation and/or transalkylation have already been described in the prior art and are based on mordenite (U.S. Pat. No. 3,506,731, U.S. Pat. No. 4,151,120, U.S. Pat. No. 4,180,693, U.S. Pat. No. 4,210,770, U.S. Pat. No. 3,281,483, U.S. Pat. No. 3,780,121, or U.S. Pat. No. 3,629,351), based on omega zeolite (U.S. Pat. No. 5,210,356, U.S. Pat. No. 5,371,311) or else based on NES-structured zeolite (EP-A-1,077,083). These catalysts do not make it possible to conduct optimal catalytic performances, in particular in terms of selectivity, in the reactions for transalkylation of alkyl-aromatic hydrocarbons.

This invention proposes providing a new catalyst that in reactions for transalkylation of alkyl-aromatic hydrocarbons leads to improved catalytic performance levels relative to the catalysts of the prior art.

SUMMARY

The catalyst of this invention contains at least one BOG-structured zeolite, in particular Boggsite, that comprises silicon and at least one element T that is selected from the group that is formed by aluminum, iron, gallium and boron. This zeolite is present at least partially in acid form. The binder is preferably alumina. The catalyst also contains at least one metal that is selected from the group that consists of the non-noble metals of groups VIB, VIIB and VIII of the periodic table. Finally, the catalyst optionally contains, in addition, at least one metal that is selected from the group that is formed by the elements of groups IIIA and IVA of the periodic table. This invention also relates to the use of the catalyst in a process for transalkylation of alkyl-aromatic hydrocarbons such as toluene and the alkyl-aromatic compounds that have at least 9 carbon atoms. This catalyst in particular is very high-performing in the treatment of C9+aromatic feedstocks that contain a percentage of aromatic molecules that have at least 10 carbon atoms that is higher than 5% by weight, whereby this feedstock can also contain benzene.

DESCRIPTION

The invention relates to a catalyst that comprises at least one binder, at least one BOG-structured zeolite, comes at least partially in acid form and comprises silicon and at least one element T that is selected from the group that is formed by aluminum, iron, gallium and boron, whereby said catalyst also comprises at least one metal that is selected from the group that consists of the non-noble metals of groups VIB, VIIB and VIII of the periodic table.

The BOG-structured zeolite, in particular Boggsite, encompassed in the catalyst according to the invention, has the characteristics of the one described in "Atlas of Zeolite Framework Types," W. M. Meier, D. H. Olson, and Ch. Baerlocher, 5$^{th}$ Revised Edition, 2001, Elsevier, to which this application refers.

The chemical composition of said BOG-structured zeolite as described in the "Atlas of Zeolite Framework Types" is: $Na^+{}_4Ca^{2+}{}_7$ $(H_2O)_{74}[Al_{18}Si_{78}O_{192}]$. Said BOG-structured zeolite is characterized by the fact that it has an x-ray diffraction diagram that comprises at least the lines that are exhibited in Table 1 (Pluth, J. and Smith, J.; American Mineralogist 75 (1990) 501-507).

TABLE 1

| 2θ | Intensity I/Imax |
|---|---|
| 7.43 | Weak |
| 7.84 | Strong |
| 8.17 | Weak |
| 8.74 | Weak |
| 11.05 | Weak |
| 13.13 | Weak |
| 15.72 | Weak |
| 18.02 | Weak |
| 19.90 | Medium |
| 20.38 | Medium |
| 21.09 | Weak |
| 22.19 | Weak |
| 22.41 | Weak |
| 23.05 | Strong |
| 23.68 | Weak |
| 24.10 | Weak |
| 24.25 | Weak |
| 24.69 | Medium |
| 25.29 | Weak |
| 26.32 | Strong |
| 26.44 | Strong |
| 26.99 | Weak |
| 27.88 | Weak |
| 27.89 | Weak |
| 28.96 | Weak |
| 29.28 | Weak |
| 30.04 | Weak |
| 31.10 | Weak |
| 31.17 | Weak |
| 32.23 | Weak |
| 33.59 | Weak |
| 34.05 | Medium |
| 34.64 | Weak |
| 37.29 | Weak |
| 44.79 | Weak |
| 45.72 | Weak |
| 45.75 | Weak |
| 46.55 | Weak |

It is found in the natural state, in particular in the state of Oregon in the U.S.A.

The BOG-structured zeolite, in particular Boggsite, has a two-dimensional microporous network that consists of channels whose pore opening is delimited by openings with 10 and 12 oxygen atoms. A pore opening with 10 or 12 oxygen atoms corresponds to pores with 10 or 12 sides. The determination of the diameter of pores that are present in the BOG-structured zeolite resulted in the following values: 7.0×7.0 Å for the pores with 12 sides and 5.5×5.8 Å for the pores with 10 sides.

When it is included in the catalyst according to the invention, the BOG-structured zeolite is at least partially, preferably virtually totally, in acid form, i.e., in hydrogen form ($H^+$). The content of alkaline and/or alkaline-earth cations is less than 0.2% by weight, preferably less than 0.05% by weight relative to the total weight of dry zeolite.

The overall Si/T atomic ratio of the BOG-structured zeolite that is present in the catalyst according to the invention is between 4 and 100, preferably between 4 and 75 and very preferably between 4 and 50.

The catalyst according to the invention contains at least one BOG-structured zeolite at a ratio of 10 to 90%, preferably 20 to 85%, and even more preferably 50 to 85% by weight and at least one matrix (or binder) made up to 100% of the catalyst, whereby said zeolite comprises silicon and at least one element T that is selected from the group that is formed by aluminum, iron, gallium and boron, preferably aluminum.

Said catalyst also comprises at least one metal that is selected from the group that consists of the non-noble metals of groups VIB, VIIB, and VIII. Said metal is advantageously present at a content of between 0.01 and 5% and preferably between 0.05 and 3% by weight. According to the invention, the preferred metal of group VIIB is rhenium, the preferred metal of group VIB is molybdenum, and the preferred non-noble metal of group VIII is nickel. Advantageously, the metal that is selected from the group that consists of the non-noble metals of groups VIB, VIIB and VIII is rhenium. The catalyst according to the invention optionally comprises at least one element that is selected from among all the elements of groups IIIA and IVA of the periodic table, preferably selected from the group that is formed by indium and tin, at a content of between 0.01 and 5% and preferably between 0.5 and 3% by weight.

The matrix, present at a content of between 10 and 90%, preferably between 15 and 80% by weight, and even more preferably between 15 and 50% by weight relative to the total weight of catalyst, is generally selected from among the elements of the group that is formed by the clays (for example, from among the natural clays such as kaolin or bentonite), magnesia, aluminas, silicas, titanium oxide, boron oxide, zirconia, aluminum phosphates, titanium phosphates, zirconium phosphates, silica-aluminas and carbon, preferably from among the elements of the group that is formed by the aluminas and clays, even more preferably from among the aluminas.

A preferred catalyst according to the invention comprises by weight, relative to the total weight of said catalyst, 10 to 90% by weight of BOG-structured zeolite, 0.01 to 5% by weight of at least one metal that is selected from the group that consists of the non-noble metals of groups VIB, VIIB and VIII, and at least one matrix made up to 100%.

The BOG-structured zeolite is present, for example, in the catalyst according to the invention in natural exchanged form. It may also have been subjected to a treatment that consists in extracting a portion of the element T from the zeolitic framework. When the element T is aluminum, the process is referred to as dealuminification. Two dealuminification methods preferably can be used, but any other method that is known to one skilled in the art is also part of the framework of the invention.

These dealuminification methods that are described below for the aluminum can also be valuable for the other elements T.

The first so-called direct acid attack method comprises a stage for treatment by an aqueous solution of a mineral acid, such as $HNO_3$ or HCl, or an organic acid, such as $CH_3CO_2H$. This last stage may be repeated as many times as it is necessary so as to obtain the desired dealuminification level. Prior to the direct acid attack stage, it is possible to carry out one or more ion exchange(s) by at least one $NH_4NO_3$ solution, for example, so as to eliminate at least partially, preferably virtually completely, the alkaline and/or alkaline-earth cations. Likewise, at the end of the dealuminification treatment by direct acid attack, it optionally is possible to carry out one or more ion exchange(s) by at least one $NH_4NO_3$ solution, so as to eliminate the residual alkaline and/or alkaline-earth cations and in particular the sodium.

To reach the desired Si/Al ratio, it is necessary to select the operating conditions well; from this standpoint, the most critical parameters are the temperature of treatment by the aqueous acid solution, the concentration of said acid, the nature of said acid, the ratio between the amount of acid solution and the mass of treated zeolite, the period of treatment and the number of treatments carried out.

It is also possible to carry out dealuminification treatments by dealuminifying chemical compounds such as (by way of example and in a non-exhaustive manner) silicon tetrachloride ($SiCl_4$), ammonium hexafluorosilicate [$(NH4)_2SiF_6$], ethylenediaminetetraacetic acid (EDTA) as well as its monosodium and disodium forms. These reagents can be used in solution or in gas phase, for example, in the case of $SiCl_4$.

The second so-called dealuminification method of heat treatment (in particular with water vapor or "steaming") followed by an acid attack comprises, in a first step, a stage in which the solid is subjected to one or more ion exchange(s) by at least one $NH_4NO_3$ solution, for example, so as to eliminate at least partially, preferably virtually totally, the alkaline and/or alkaline-earth cations, in particular sodium, that are present in cationic position in the zeolite. The zeolite that is thus obtained is subjected to at least one framework dealuminification cycle that comprises at least one heat treatment that is carried out, optionally and preferably in the presence of water vapor, at a temperature of generally between 500 and 900° C., and optionally followed by at least one acid attack by an aqueous solution of a mineral or organic acid. The calcination conditions in the presence of water vapor (temperature, water vapor pressure and duration of treatment) as well as the post-calcination acid attack conditions (duration of the attack, concentration of the acid, nature of the acid that is used and ratio between the acid volume and the zeolite mass) are adapted so as to obtain the desired dealuminification level. For the same purpose, it is also possible to operate on the number of heat treatment-acid attack cycles that are carried out.

A variant of this second method may consist in replacing the so-called acid attack stage, i.e., the treatment by an acid solution, by a treatment by a solution of a dealuminifying chemical compound, such as, for example, those cited above, namely silicon tetrachloride ($SiCl_4$), ammonium hexafluorosilicate [$(NH4)_2SiF_6$], ethylenediaminetetraacetic acid (EDTA) as well as its monosodium and disodium forms.

In the preferred case where the element T is aluminum, the dealuminification cycle of the framework, comprising at least one heat treatment stage that is carried out, optionally and preferably, in the presence of water vapor and at least one attack stage in acid medium of the BOG-structured zeolite, can be repeated as many times as it is necessary to obtain the dealuminified BOG-structured zeolite that has the desired characteristics. Likewise, following the heat treatment that is carried out, optionally and preferably in the presence of water vapor, several successive acid attacks, with acid solutions of various concentrations, can be performed.

A variant of this second dealuminification method comprises the heat treatment of the BOG-structured zeolite at a temperature of generally between 500° C. and 900° C., optionally and preferably in the presence of water vapor. Then, the zeolite is optionally treated by at least one aqueous solution of a mineral acid (for example $HNO_3$ or HCl) or an organic acid ($CH_3CO_2H$, for example). Finally, the solid that is thus obtained optionally can be subjected to at least one ion exchange by at least one $NH_4NO_3$ solution, for example, so as to eliminate virtually any alkaline and/or alkaline-earth cation, in particular sodium, that is present in a cationic position in the zeolite.

The catalyst according to the invention can be prepared according to any method that is known to one skilled in the art. In general, it is obtained by mixing the matrix and the BOG-structured zeolite, then by shaping. The metal that is selected from the group that consists of the non-noble metals of groups VIB, VIIB and VIII can be introduced either before the shaping or else during the mixing, or else, and preferably, after the shaping. It is thus understood that the matrix+zeolite mixture is a substrate for the catalyst that contains the metal that is selected from the group that consists of the non-noble metals of groups VIB, VIIB and VIII. The shaping is generally followed by a calcination, generally at a temperature of between 250 and 600° C. The metal that is selected from the group that consists of the non-noble metals of groups VIB, VIIB and VIII can be introduced after said calcination. In all of the cases, said metal is generally deposited, as desired, either virtually totally on the zeolite, or virtually totally on the matrix, or partially on the zeolite and partially on the matrix, whereby this selection is carried out in a way that is known to one skilled in the art, by the parameters that are used during said deposit, such as, for example, the nature of the precursor that is selected to carry out said deposit.

The metal that is selected from the group that consists of the non-noble metals of groups VIB, VIIB and VIII, preferably rhenium, therefore can be deposited on the zeolite-matrix mixture shaped in advance by any process that is known to one skilled in the art. Such a deposit is generally carried out by the dry-impregnation technique, with ion exchange(s) or co-precipitation. Among the precursors, it is possible to cite in a non-limiting manner perrhenic acid and ammonium perrhenate, deposited by, for example, dry impregnation.

The deposit of the metal that is selected from the group that consists of the non-noble metals of groups VIB, VIIB and VIII is followed in general by a calcination in air or oxygen, generally between 300 and 600° C., preferably between 350 and 550° C., and for a duration of between 0.5 and 10 hour(s), preferably between 1 and 4 hour(s).

In the case where the catalyst contains several metals, the latter can be introduced either all in the same way or by different techniques, before or after shaping and in any order. In the case where the technique that is used is that of ion exchange, several successive exchanges may be necessary to introduce the required amounts of metals.

The shaping of the catalyst according to the invention is generally such that the catalyst is in the form of pellets, aggregates, extrudates or balls, with a view to its use, preferably in the form of extrudates or balls.

For example, one of the preferred methods for preparing the catalyst according to the invention consists in mixing the zeolite in a moist matrix gel (generally obtained by mixing at least one acid and a matrix powder), for example alumina, for a necessary duration to obtain a good homogeneity of the thus obtained paste, or, for example, for about 10 minutes, then in passing said paste through a die to form extrudates, for example with a diameter of between 0.4 and 4 mm. Then, after drying for several hours at 100° C. in an oven and after calcination, for example for 2 hours at 400° C., the metal, for example rhenium, can be deposited, for example by dry impregnation of an ammonium perrhenate solution, whereby said deposit is followed by a final calcination, for example for 2 hours at 400° C. The catalyst that is obtained is preferably characterized by a macroscopic distribution coefficient of the metal, obtained from its profile that is determined by Castaing microprobe, defined as the ratio of the concentrations of said metal in the core of the grain relative to the edge of this same grain, preferably encompassed between 0.7 and 1.3, inclusive. Moreover, the catalyst according to this invention, in the form of balls or extrudates, preferably exhibits a bed crushing value, determined according to the Shell method (SMS 1471-74) to be higher than 0.7 MPa.

The preparation of the catalyst generally ends in a calcination, said final calcination, usually at a temperature of between 250 and 600° C., preferably preceded by a drying, for example, in the oven, at a temperature of generally between ambient temperature and 250° C., preferably between 40 and 200° C. Said drying stage is preferably conducted during the rise in temperature that is necessary to carry out said calcination.

It is then possible to initiate a reduction under hydrogen, generally at a temperature of between 300 and 600° C., preferably between 350 and 550° C., and for a duration of between 1 and 10 hour(s), preferably between 2 and 5 hours. Such a reduction can take place ex situ or in situ, relative to the place of use of said catalyst in a given reaction.

The catalyst of this invention optionally can contain sulfur. In this case, the sulfur is introduced onto the catalyst that is shaped, calcined and that contains the element or elements cited above, either in situ before the catalytic reaction, or ex situ. The sulfurization is carried out by using any sulfurizing agent that is well known to one skilled in the art, such as, for example, the dimethyl disulfide or the hydrogen sulfide. The operational sulfurization occurs after the reduction. In the case of an in situ sulfurization, the reduction, if the catalyst has not been reduced in advance, takes place before the sulfurization. In the case of a sulfurization ex situ, the reduction and then the sulfurization are carried out.

Another object of the invention is the use of the catalyst according to the invention that contains at least one BOG-structured zeolite, in particular Boggsite, in hydrocarbon conversion processes.

In particular, the invention relates to the use of said catalyst for transalkylation of alkyl-aromatic hydrocarbons, and preferably the transalkylation of toluene and alkyl-aromatic hydrocarbons generally into $C_9^+$ (i.e., with at least 9 carbon atoms per molecule), with toluene-$AC_9^+$ mixtures (where $AC_9^+$ designates the alkyl-aromatic hydrocarbons that comprise at least 9 carbon atoms per molecule) that can contain 0 to 100% of $AC_9^+$ relative to the total mixture. Said catalyst proves very effective for said use, because it proves particularly active, selective and stable, even in the presence of feedstocks to be treated that contain a large amount of heavy aromatic compounds $AC_9^+$, whereby these heavy aromatic compounds can contain a large proportion of $AC_{10}^+$. Thus, $AC_9^+$ feedstocks that contain at least 5% and up to 25% by weight, and even more $AC_{10}^+$ can be upgraded. By way of examples, it is possible to cite in a non-exhaustive manner the dimethylethylbenzenes, the diethylbenzenes, the propylethylbenzenes . . . . The use of this catalyst for transalkylation of heavy alkyl-aromatic compounds is therefore particularly advantageous.

The operating conditions for said use are generally as follows: a temperature of between 250 and 650° C. and preferably between 350 and 550° C.; a pressure of between 1 and 6 MPa and preferably between 2 and 4.5 MPa; a feed volumetric flow rate, expressed in kilograms of feedstock introduced per kilogram of catalyst and per hour, of between 0.1 and 10 $h^{-1}$ and preferably between 0.5 and 4 $h^{-1}$; a hydrogen to hydrocarbons molar ratio of between 2 and 20 and preferably between 3 and 12 mol/mol.

EXAMPLES

Example 1

Preparation of a Catalyst Based on Boggsite Zeolite and Rhenium, in Accordance with the Invention

The raw material that is used is a Boggsite zeolite (Oregon, USA) that has an overall Si/Al atomic ratio that is equal to 4.3, and a content by weight of cations (sodium, calcium) relative to the weight of dry Boggsite zeolite of about 6.0%.

This Boggsite zeolite is subjected to four successive ion exchanges in a 10N $NH_4NO_3$ solution at about 100° C. for 4 hours so as to withdraw the residual sodium and calcium. Between each exchange, the zeolite is dried for one night at 100° C.

At the end of these treatments, the Boggsite zeolite in H form has an overall Si/Al atomic ratio that is equal to 4.7, and a content by weight of cations (sodium, calcium) relative to the dry Boggsite zeolite weight of 1100 ppm.

This zeolite is then shaped by extrusion with an alumina gel so as to obtain, after drying and calcination under dry air, a substrate S1 that contains 70% by weight of Boggsite zeolite in H form and 30% alumina.

The S1 substrate is then impregnated with an aqueous solution of perrhenic acid, so as to deposit 0.3% by weight of rhenium on the solid. The moist solid is then dried at 120° C. for 12 hours and calcined under a flow of dry air at the temperature of 500° C. for one hour. The catalyst C1 that is thus obtained contains 69.7% by weight of Boggsite, 30% by weight of alumina, and 0.3% by weight of rhenium.

Example 2

Preparation of a Catalyst Based on Boggsite Zeolite and Nickel, in Accordance with the Invention

In this example, substrate S1 that is described in Example 1 and that contains 70% by weight of Boggsite zeolite in H form and 30% alumina is used.

Substrate S1 is subjected to a dry impregnation by a nickel nitrate solution so as to deposit 0.3% by weight of nickel on the solid. The moist solid is then dried at 120° C. for 12 hours and calcined under a flow of dry air at the temperature of 500° C. for one hour. The catalyst C2 that is thus obtained contains 69.8% by weight of Boggsite, 29.9% of alumina and 0.3% of nickel.

Example 3

Preparation of a Catalyst Based on NU-87 Zeolite and Rhenium, Not in Accordance with the Invention

The raw material that is used is ari NU-87 zeolite that has an overall Si/Al atomic ratio that is equal to 17.2, whereby a content by weight of sodium corresponds to an Na/Al atomic ratio that is equal to 0.14. This NU-87 zeolite was synthesized according to European Patent Application EP-A-0,377,291 or Patent EP-B-0,378,916.

This NU-87 zeolite first undergoes a so-called dry calcination at 550° C. under a stream of air and nitrogen for 6 hours. Then, the solid that is obtained is subjected to an ion exchange in a 10N $NH_4NO_3$ solution at about 100° C. for 4 hours. The NU-87 zeolite is then subjected to a treatment by a 7N nitric acid solution, at about 100° C., for 5 hours. Volume V of the nitric acid solution that is used (in ml) is equal to 10×weight P of dry NU-87 zeolite (VIP=10). This treatment by a 7N nitric acid solution is carried out a second time under the same operating conditions.

At the end of these treatments, the zeolite that is obtained is found in its H form and has an overall atomic Si/Al ratio that is equal to 34.6, and an Na/Al ratio that is equal to 0.007.

The H-NU-87 zeolite is then shaped by extrusion with an alumina gel so as to obtain, after drying and calcination under dry air, the substrate S2 that contains 70% by weight of H-NU-87 zeolite and 30% alumina.

Substrate S2 is impregnated with an aqueous solution of ammonium perrhenate so as to deposit 0.3% by weight of rhenium on the solid. The moist solid is then dried at 120° C. for 12 hours and calcined under a stream of dry air at the temperature of 500° C. for one hour. Catalyst C3 that is thus obtained contains 69.8% by weight of NU-87 in hydrogen form, 29.9% of alumina and 0.31% of rhenium.

Example 4

Comparison of Catalytic Performance Levels of Catalysts C1 and C3

The catalysts are reduced under hydrogen in advance at 450° C. for 2 hours. The catalytic tests were carried out under the following operating conditions:

temperature: 450° C.

total pressure: 3 MPa

H2/HC: 5 mol/mol.

A feedstock $AC_9^+$, noted A1, containing 83.0% by weight of aromatic compounds with 9 carbon atoms and 17.0% by weight of aromatic compounds with 10 carbon atoms has been used.

The two catalysts that contain rhenium, one based on Boggsite zeolite (C1 according to the invention) and the other based on NU-87 zeolite (C3 not according to the invention) were compared in iso-conversion with a feedstock that contains 20% of toluene and 80% of A1 feedstock. The results are presented in Table 2:

TABLE 2

| Feedstock | 20% Toluene/80% A1 | |
|---|---|---|
| Catalysts | C1 | C3 |
| | (According to the Invention) | (Not According to the Invention) |
| Overall Conversion (%) | 54.9 | 54.9 |
| Yields (% by Weight) | | |
| $C_1$-$C_4$ Light Products | 11.6 | 12.2 |
| $C_5^+$ | 0.8 | 1.1 |
| Benzene | 5.8 | 5.5 |
| Xylenes | 34.8 | 34.1 |
| Ethylbenzene | 0.9 | 0.7 |
| Heavy Products | 0.9 | 1.3 |

These results make it possible to show the better selectivity of the catalyst based on Boggsite. Actually, the xylene yield is increased while the yield of $C_5^+$, undesired secondary products of the reaction, decreases. Some of the compounds of this $C_5^+$ fraction are detrimental to the purity of the benzene that is produced. In addition, this $C_5^+$ fraction essentially contains paraffins with 5 and 6 carbon atoms that are obtained from aromatic cycles (opening and cracking). There is therefore an increased loss of aromatic cores and consequently a loss of products that are desired in the case of catalyst C3, not in accordance with the invention.

The invention is claimed is:

1. A Catalyst that comprises at least one binder, at least one BOG-structured zeolite, at least partially in acid form and comprising silicon and at least one element T selected from the group consisting of aluminum, iron, gallium and boron, wherein said catalyst also comprises at least one metal from the non-noble metals of groups VIB, VIIB or VIII of the periodic table.

2. A Catalyst according to claim 1, wherein the metal from the the non-noble metals of groups VIB, VIIB or VIII of the periodic table is rhenium.

3. A Catalyst according to claim 2 wherein the BOG-structured zeolite is Boggsite zeolite.

4. A Catalyst according to claim 2 wherein the element T is aluminum.

5. A Catalyst according to claim 3 wherein the element T is aluminum.

6. A Catalyst according to claim 5 further comprising at least one element of groups IIIA or IVA of the periodic table.

7. A Catalyst according to claim 6, wherein the element from the elements of groups IIIA and IVA is indium or tin.

8. A Catalyst according to claim 6 comprising 0.01 to 5% of at least one element from groups IIIA or IVA.

9. In a hydrocarbon catalytic conversion process the improvement wherein the catalyst is that of claim 7.

10. A Catalyst according to claim 1 wherein the BOG-structured zeolite is Boggsite zeolite.

11. A Catalyst according to claim 10 wherein the element T is aluminum.

12. A Catalyst according to claim 1 wherein the element T is aluminum.

13. A Catalyst according to claim 1 further comprising at least one element of groups IIIA or IVA of the periodic table.

14. A Catalyst according to claim 13, wherein the element from the elements of groups IIIA and IVA is indium or tin.

15. A Catalyst according to claim 1 further comprising sulfur.

16. A Catalyst according to claim 1 comprising by weight, relative to the total weight of catalyst, 10 to 90% by weight of BOG-structured zeolite, 0.01 to 5% by weight of at least one metal selected from the group consisting of the non-noble metals of groups VIB, VIIB and VIII, and at least one matrix made up to 100%.

17. In a hydrocarbon catalytic conversion process the improvement wherein the catalyst is that of claim 1.

18. A process according to claim 17, wherein said process is a process for transalkylation of an alkyl-aromatic hydrocarbon feedstock.

19. A process according to claim 18 for transalkylation of toluene and alkyl-aromatic hydrocarbons.

20. A process according to claim 18 for the treatment of aromatic feedstocks that contain at least 5% by weight of aromatic compounds having at least 10 carbon atoms.

* * * * *